United States Patent
Yavitz

[19]

[11] Patent Number: 6,161,546
[45] Date of Patent: *Dec. 19, 2000

[54] SYSTEM FOR ALTERING TISSUE BENEATH AN OUTER LAYER OF TISSUE

[75] Inventor: Edward Q. Yavitz, Rockford, Ill.

[73] Assignee: Quardrivium, L.L.C., Phoenix, Ariz.

[ * ] Notice: This patent is subject to a terminal disclaimer.

[21] Appl. No.: 09/078,368

[22] Filed: May 13, 1998

Related U.S. Application Data

[63] Continuation-in-part of application No. 08/858,967, May 20, 1997, Pat. No. 6,009,876, which is a continuation-in-part of application No. 08/852,360, May 7, 1997, Pat. No. 5,820,624, which is a continuation-in-part of application No. 08/503,101, Jul. 17, 1995, Pat. No. 5,649,922.

[51] Int. Cl.[7] ................................................ A61B 19/00
[52] U.S. Cl. ............................... 128/898; 606/10
[58] Field of Search ............................. 128/898; 606/1, 606/4, 5, 6, 10, 11, 14, 2, 3, 9, 12, 13, 15–19; 607/89, 88, 90, 94

[56] References Cited

U.S. PATENT DOCUMENTS

| | | |
|---|---|---|
| 3,074,407 | 1/1963 | Moon et al. . |
| 4,156,124 | 5/1979 | Macken et al. . |
| 4,406,285 | 9/1983 | Villasenor et al. . |
| 4,461,294 | 7/1984 | Baron . |
| 4,840,175 | 6/1989 | Peyman . |
| 4,903,695 | 2/1990 | Warner et al. . |
| 4,905,711 | 3/1990 | Bennett et al. . |
| 4,976,709 | 12/1990 | Sand . |
| 5,057,104 | 10/1991 | Chess . |
| 5,092,863 | 3/1992 | Schanzlin . |
| 5,108,412 | 4/1992 | Krumeich et al. . |
| 5,137,530 | 8/1992 | Sand . |
| 5,282,797 | 2/1994 | Chess . |
| 5,312,395 | 5/1994 | Tan et al. . |
| 5,336,215 | 8/1994 | Hsueh et al. . |
| 5,356,409 | 10/1994 | Nizzola . |
| 5,437,657 | 8/1995 | Epstein . |
| 5,486,172 | 1/1996 | Chess . |
| 5,582,608 | 12/1996 | Brown . |
| 5,611,795 | 3/1997 | Slatkine et al. . |
| 5,616,139 | 4/1997 | Okamoto . |
| 5,649,922 | 7/1997 | Yavitz . |
| 5,820,624 | 10/1998 | Yavitz .......................................... 606/4 |
| 6,009,876 | 1/2000 | Yavitz ..................................... 128/898 |

FOREIGN PATENT DOCUMENTS

| | | |
|---|---|---|
| 0531756 | 3/1993 | European Pat. Off. . |
| WO92/01430 | 2/1992 | WIPO . |
| WO92/10152 | 6/1992 | WIPO . |
| WO94/18920 | 9/1994 | WIPO . |
| WO95/15134 | 6/1995 | WIPO . |

*Primary Examiner*—V. Millio
*Assistant Examiner*—Kelley O'Hara
*Attorney, Agent, or Firm*—Fletcher, Yoder & Van Someren

[57] ABSTRACT

A system allows treatment of sublayers of tissue lying beneath an outer layer of tissue. The system includes an energy emitter able to heat predetermined areas of the tissue sublayers. The energy for heating typically is generated by a laser or lamp able to produce electromagnetic radiation in the infrared region to thereby cause tissue at the predetermined areas to heat and shrink. The shrinkage causes the shape of the outer layer or surface to change in a controlled manner that corrects the problematic surface formation, e.g., refractive error. An energy absorption modifier is used to avoid damage to the outer layer of tissue as energy is passed therethrough.

12 Claims, 4 Drawing Sheets

SYSTEM FOR ALTERING TISSUE BENEATH AN OUTER LAYER OF TISSUE

This is a continuation-in-part of U.S. patent application, Method for Modifying and Reshaping Collagen Beneath the Surface of the Skin, Ser. No. 08/858,967, filed May 20, 1997, now U.S. Pat. No. 6,009,876 and U.S. patent application, System for Altering Corneal Tissue, Ser. No. 08/852,360, filed May 7, 1997, now U.S. Pat. No. 5,820,624 the latter application being a continuation-in-part of U.S. patent application, Apparatus and Method for Altering Corneal Tissue, Ser. No. 08/503,101, filed on Jul. 17, 1995, now U.S Pat. No. 5,649,922.

FIELD OF THE INVENTION

The present invention relates generally to a system for improving the shape and/or appearance of an outer layer of tissue, and particularly to an energy source and energy absorption modifier that stimulate tissue beneath an outer layer of tissue without damaging the outer layer.

BACKGROUND OF THE INVENTION

Heat has long been used to modify and reshape collagen beneath the surface of the skin. Egyptians used salt, oil and alabaster to improve skin texture and Turks used fire to singe the surface of the skin. In the twentieth century, chemical peels implementing phenol and trichloacetic acid were introduced to reduce wrinkles and remove other anomalies of the skin. Lasers, such as carbon dioxide lasers, were also developed and used for the reduction or elimination of wrinkles, such as periorbital wrinkles, and other anomalies of the skin. Such methods were more or less effective in reducing or eliminating wrinkles by providing energy in the form of heat to the subreticular dermis between the epidermis and the dermis of an individual's skin. Heat stimulates release of factors that promote new collagen growth and a thicker healthier matrix of elastins and collagen to provide a younger looking skin. However, these techniques result in removal, destruction or damage to the epidermis proximate the area in which heat is applied to the subreticular dermal layer. The damage or destruction of the epidermis results in redness, loss of body fluid and a greater potential for infection.

For example, with lasers, laser light energy is used to heat tissue beneath the epidermis, but the laser light energy must pass through the epidermis on its way to the treatment area. This laser light energy is absorbed by the epidermis as it passes therethrough and generates unwanted heat that effectively ablates the epidermal layer in the area of treatment. After time, the epidermis heals and grows back over the treatment area.

Attempts have been made to minimize injury to the epidermis by removing heat from the epidermal area proximate the area of treatment. This is typically accomplished by delivering a coolant to the epidermis at the area where it is penetrated by the laser beam. However, this adds to the complexity of the equipment and the procedure.

Additionally, refractive errors, such as nearsightedness and farsightedness, can be reduced or corrected by reshaping the cornea of an eye. There are currently many methods for reshaping the cornea, including laser radial keratotomy and scalpel radial keratotomy. One problem with these procedures, particularly in correcting farsightedness, is the difficulty of gauging the effects of making incisions in the corneal surface.

One new technique involves heating the middle of the cornea in a radial pattern with a holmium laser. The heating causes the central cornea to bulge forward, thereby temporarily correcting for farsightedness. Unfortunately, the effect of the holmium laser alone is not permanent. Moreover, it is difficult to contain the laser to only those areas that are to be heated. Most energy sources for providing heat, such as the holmium laser, pulsed infrared light sources and even low wavelength lasers having wavelengths on the order of 1320 nanometers, are absorbed first by the outermost epithelial layer of the cornea before reaching the inner layers of the cornea where the desired reshaping should occur. The absorption of energy by the epithelial layer causes damage to the epithelium that results in pain and permeability to bacteria.

It would be advantageous to have a system for permanently reshaping the sublayers of tissue to correct surface layer defects.

SUMMARY OF THE INVENTION

The present invention features a system for altering tissue that resides beneath an outer layer of tissue, such as an epidermis or epithelium. The system comprises an energy absorption modifier applied to a portion of a specific outer tissue layer of the individual. The system further includes an energy emitter for directing energy through a portion of the outer tissue layer of the individual and heating a desired area of the underlying tissue. The heating is accomplished via absorption of energy at the desired area without causing detrimental heat buildup in the outer tissue layer.

According to one aspect of the invention, a liquid composition is provided for application to an outer tissue layer, e.g. the epidermis or epithelium, of an individual to reduce the absorption of certain types of electromagnetic energy that are passed through this outer layer via the energy emitter. The energy absorption modifier is formulated to displace at least some of the naturally occurring water within the portion of the outer tissue layer, and may comprise deuterium oxide or tritium oxide. Additionally, an ultrasonic emitter may be used to facilitate diffusion of the energy absorption modifier or other materials into the tissue.

BRIEF DESCRIPTION OF THE DRAWINGS

The invention will hereafter be described with reference to the accompanying drawings, wherein like reference numerals denote like elements, and.

DETAILED DESCRIPTION OF THE PREFERRED EMBODIMENTS

The present invention includes a system by which the outermost layer of a body can be protected while internal tissues are altered, typically by heating. The following discussion will focus on protection of the epidermis of the skin and the epithelium of the eye during treatment of underlying tissue, but this system can also be used on other regions of the body.

Figure 1:
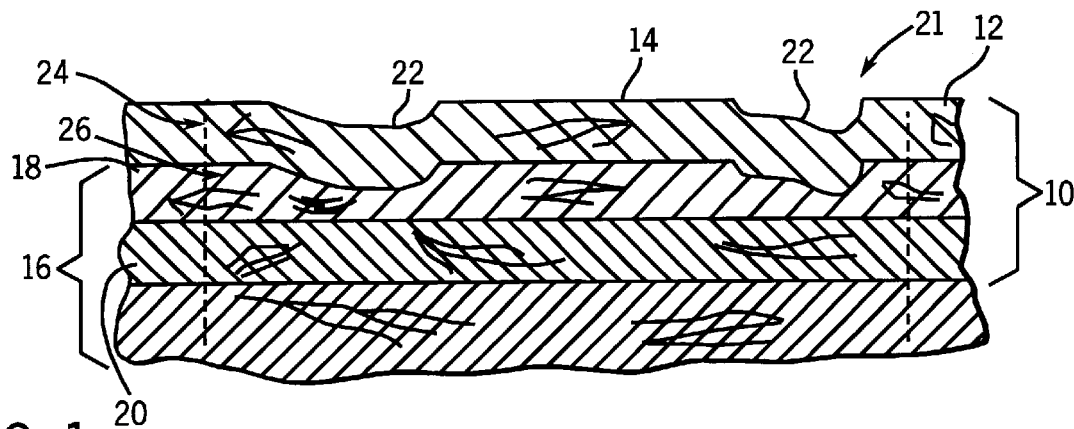
FIG. 1 is a cross-sectional view of a portion of an individual's skin.

Referring generally to FIG. 1, a cross-section of a portion of human skin 10 is illustrated. The skin includes an outer epidermal layer or epidermis 12 having an outer surface 14. Outer surface 14 is the visible surface of an individual's skin.

Additional tissue 16 is disposed beneath epidermis 12 and includes layers of skin 10 as well as deeper tissue. For example, skin 10 includes a subreticular dermal layer 18 disposed between epidermis 12 and a dermal layer or dermis 20.

In FIG. 1, skin 10 is illustrated as having an anomaly 21, such as wrinkles 22, disposed along a portion 24 of epidermis 12. One way of improving the appearance of skin 10, and particularly portion 24 of epidermis 12, is to heat an area of tissue 16 disposed beneath portion 24. In particular, it is desirable to sufficiently heat a desired treatment area 26 of subreticular dermal layer 18. Heating treatment area 26 tends to shrink wrinkles 22 and stimulate the release of factors that promote new collagen growth and a thicker healthier matrix of elastins and collagen that provide skin 10 with a younger, healthier appearance. This wrinkle reduction effect is also achieved with conventional laser treatment techniques.

Figure 2:
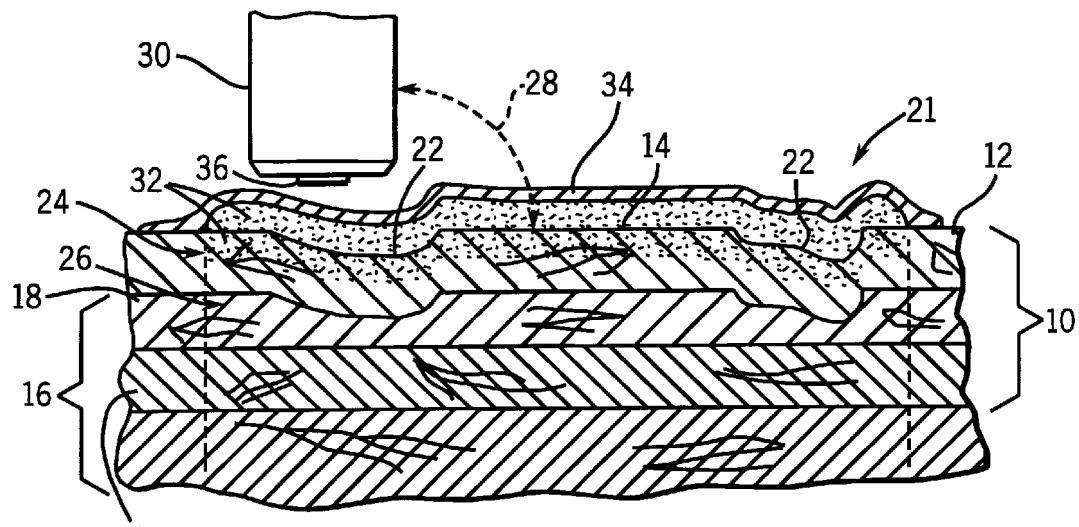
FIG. 2 is a cross-sectional view similar to FIG. 1 but with an energy absorption modifier applied.

Referring now to FIG. 2, a system 28 according to a preferred embodiment of the present invention, is illustrated. System 28 includes an energy emitter 30, an energy absorption modifier 32 and a protectant layer 34 disposed over energy absorption modifier 32 after it is applied to portion 24 of epidermis 12.

Energy emitter 30 preferably emits energy in the form of electromagnetic radiation that can be absorbed by tissue 16, e.g., at desired treatment area 26 of subreticular dermal layer 18, to create heat within that tissue area. In the preferred embodiment, energy emitter 30 is a light emitter, such as a carbon monoxide laser or an Nd:YAG laser having a wavelength of approximately 1320 nanometers. Energy emitter 30 also can comprise a CO laser emitting electromagnetic radiation having a wavelength in the range from approximately 2000 to 7000 nanometers. Alternately, energy emitter 30 can be a non-laser light emitter, such as an infrared light emitter and specifically a pulsed infrared lamp. For example, energy emitter 30 may include a mercury/CO lamp capable of emitting electromagnetic radiation having a wavelength in the range from approximately 2000 to 7000 nanometers.

If a laser light energy emitter is used, it can be mounted on a mechanical carrier or hand-held by a person providing the skin rejuvenation treatment. In either case, the energy emitter 30 is oriented to direct energy through portion 24 of epidermis 12 to the desired treatment area, such as area 26. The energy emitter 30 is moved along outer surface 14 of portion 24 until the area of anomaly 21 has been fully treated and the anomaly, e.g. wrinkles 22, has been reduced or eliminated. Handling and movement of the laser is comparable to the procedures currently employed by those conducting conventional laser treatments.

Potentially, the laser light can be diffused over a greater area, or a large infrared lamp can be used to direct energy toward a relatively large portion of epidermis 12 for absorption by a relatively large desired treatment area 26. In fact, the energy may be provided by multiple infrared lamps distributed through, for example, a tanning bed to promote widespread reinvigoration of skin. Of course, the time of exposure to energy from energy emitter 30 will vary depending on the intensity of the energy and the area over which it is spread.

Energy absorption modifier 32 is a material formulated to cooperate with epidermis 12 to permit light energy, such as laser light from a carbon monoxide or Nd:YAG laser or light from an infrared lamp, to pass through portion 24 of epidermis 12 with reduced or no absorption of the energy by the naturally occurring water in the tissue of epidermis 12. This permits treatment of tissue beneath the epidermis via appropriate lasers or infrared emitters (see FIG. 3) without detrimental heat buildup in portion 24 of epidermis 12. Thus, there is minimal, if any, damage or ablation of portion 24. Additionally, because energy absorption by epidermis 12 is reduced or eliminated, it often is not necessary to continuously remove heat from portion 24 via a coolant. This improves the safety and effectiveness of skin rejuvenation with the aid of lasers or other energy emitters designed to stimulate tissue beneath the epidermal layer.

Preferably, energy absorption modifier 32 is formulated to displace the naturally occurring water ($H_2O$) within portion 24 when applied to epidermis 12. This water within the epidermal layer absorbs energy from certain lasers or other energy emitters, such as those described above, and results in the damaging heat buildup within epidermis 12. By displacing some or all of this naturally occurring water within portion 24 of epidermis 12, the energy from these types of energy emitters is permitted to pass through the epidermal layer to the subreticular dermal layer 18 or other tissue beneath epidermis 12. The result is reduced heat buildup in portion 24 of epidermis 12 during the treatment procedure. The epidermis remains intact which lessens the chance of infection, decreases redness and loss of body fluid and substantially shortens the healing time.

Figure 3:
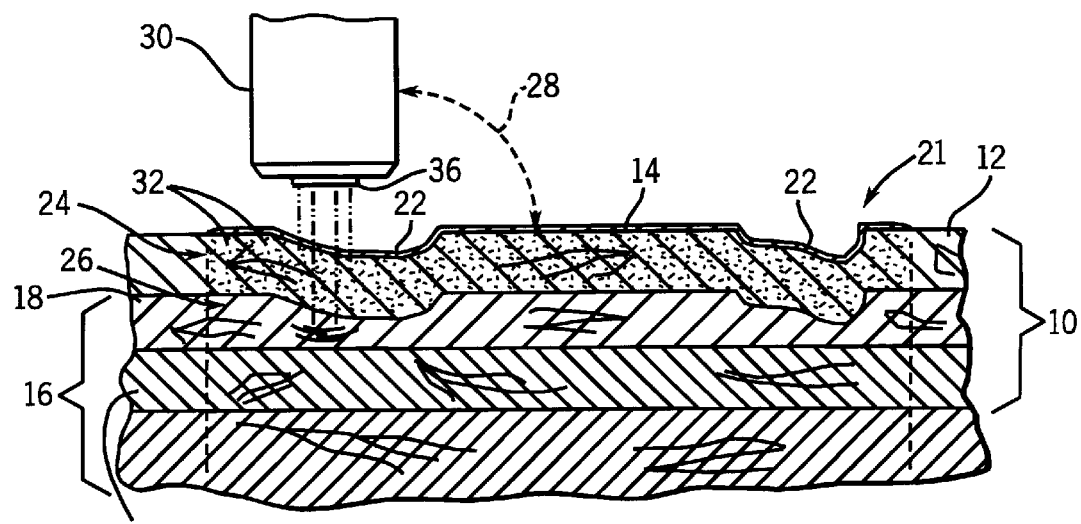
FIG. 3 is a cross-sectional view similar to that of FIG. 2 but also showing a light emitter interacting with the tissue beneath the epidermis.

Energy absorption modifier 32 typically is in liquid form and preferably comprises deuterium oxide ($D_2O$), an isotopic variant of the primary $H_2O$ isotope naturally occurring in the tissue. In an alternate embodiment, energy absorption modifier 32 comprises tritium oxide, another isotopic variant of the primary $H_2O$ isotope naturally occurring in the tissue. Both of these materials are able to displace the primary naturally occurring water content of the epidermis or the epithelium of the eye to permit energy to pass through to tissues beneath this outer layer, as best illustrated in FIG. 3.

After energy absorption modifier 32 is applied to portion 24 of epidermis 12, it typically is covered by protectant layer 34. With certain chemicals, such as deuterium oxide, evaporation occurs relatively rapidly and protectant layer 34 helps prevent this occurrence as energy absorption modifier 32 is absorbed by epidermis 12 to displace the water content in portion 24. Typically, protectant layer 34 is impermeable or semi-permeable to air. For example, protectant layer 34 can be a sheet of plastic applied over energy absorption modifier 32 and epidermis 12. Potentially, energy can be directed through protectant layer 34 toward the desired treatment area 26, but it is preferred that protectant layer 34 be removed prior to stimulating the desired treatment area 26 via energy emitter 30.

In practicing the invention, dead skin cells typically are exfoliated from epidermis 12 along outer surface 14 of portion 24. Dilute glycolic acid, alphahydroxy or citric acid can be used to exfoliate the dead skin. Following exfoliation, energy absorption modifier 32 is applied to portion 24 and covered by protectant layer 34. Energy absorption modifier 32 is provided sufficient time to be absorbed by portion 24, thereby displacing the water normally within that part of the epidermal layer. The protectant layer 34 is then removed and energy emitter 30 is used to direct energy through portion 24 to desired treatment area 26. As with conventional techniques, the energy supplied to desired treatment area 26 must sufficiently heat the area to shrink wrinkles and stimulate the release of factors that promote new collagen growth. After treatment of area 26, the epidermis 12 remains intact and the individual is left with healthier, younger looking skin.

It should be noted that a variety of energy emitters may be used, the intensity of the energy and time over which it is directed against the skin of an individual will vary depending on the degree and type of the anomalies, e.g., wrinkles, being treated. Although this system may most readily be used to reduce or eliminate wrinkles in various locations of an individual's face, the system can be used to modify and reshape collagen beneath the outer surface of the body in other areas, including an individual's eyes. Additionally, the energy absorption modifier can be formulated in several different ways. For example, it can include conventional carrier ingredients such as those found in commonly used lotions or it can be mixed with an exfoliant to permit combination of exfoliation and application of the energy absorption modifier.

In an alternate embodiment, the diffusion of energy absorption modifier 32 may be facilitated via the use of ultrasonic waves. This ultrasonic energy is used to drive the energy absorption modifier material 32 into portion 24 of the tissue layer more quickly and more deeply than that attained by normal gradient diffusion. An ultrasonic emitter 36, such as an ultrasonic probe, is used to provide and direct the ultrasonic energy towards the energy absorption modifier 32 after it is applied to the subject tissue. The ultrasonic energy drives the material into the tissue.

In the illustrated embodiment, ultrasonic emitter 36 is a probe combined with energy emitter 30, although the two emitters also can be separate devices. Furthermore, ultrasonic emitter 36 can be utilized to aid in the diffusion of other materials, such as medications, applied to an area of tissue. Typically, such materials are in liquid form, and the ultrasonic energy is used to facilitate diffusion of the material into the subject tissue.

Figure 4:
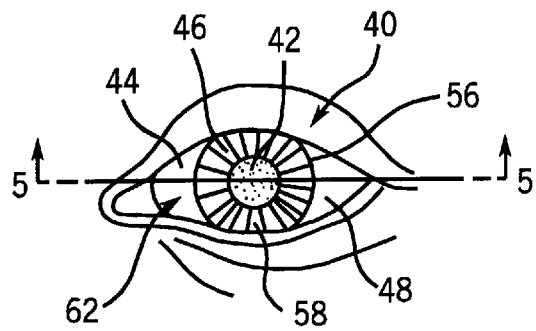
FIG. 4 is a front view of an eye that illustrates the cut portion of corneal tissue.

The above-described invention also can be utilized to treat tissue located beneath the outer epithelial layer of an eye in a fashion analogous to the preceding discussion with respect to skin. As illustrated in FIG. 4, an eye 40 includes a pupil 42 surrounded by corneal tissue 44 and, for example, an iris 46. Corneal tissue 44 is bounded by a corneal surface 48.

Many vision disorders, such as nearsightedness and farsightedness, result from a slightly misshapen corneal surface 48. Theoretically, such disorders should be correctable by reshaping corneal surface 48 to compensate for the refractive errors causing the sight disorder.

Figure 5:
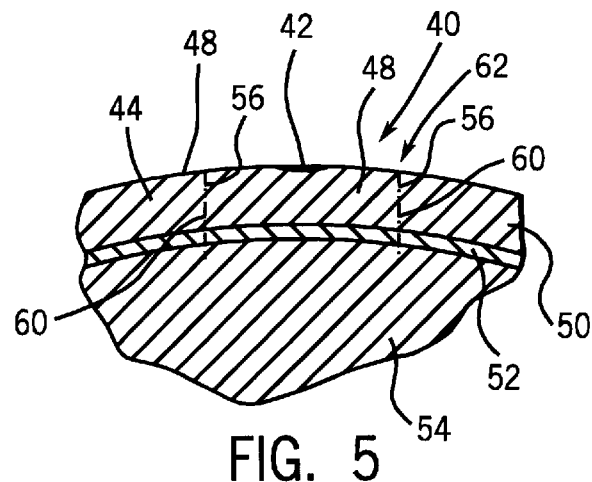
FIG. 5 is a cross-sectional view taken generally along line 5—5 of FIG. 4.

As illustrated in FIG. 5, eye 40, particularly corneal tissue 44, includes a plurality of layers between corneal surface 48 and a more central region of the eye that includes, for instance, the lens of the eye (not shown). An epithelium or epithelial layer 50 is bounded by corneal surface 48. Inwardly from epithelial layer 50 is a membrane layer 52, known as Bowman's membrane layer. Inwardly from membrane layer 52 is a collagen layer 54 that extends towards the center of the eye.

Initially, a first approach will be described in which a cut 56 is made into eye 40 through corneal surface 48, and preferably through epithelial layer 50 and membrane layer 52. Cut 56 is illustrated in FIGS. 4 and 5 and preferably extends substantially about pupil 42. According to one embodiment of the invention, cut 56 may be circular and extend in a circular pattern about pupil 42 at a given distance from pupil 42. Thus, cut 56 generally forms a plug portion 58 defined by an outer cut surface 60.

Figure 6A:
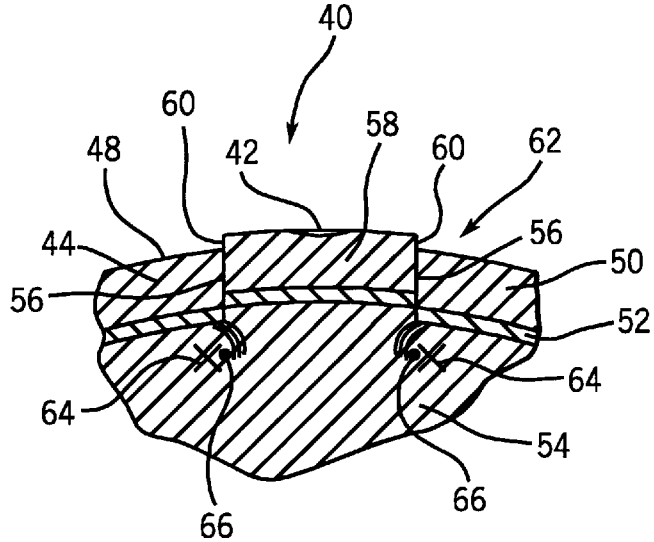
FIG. 6A is a cross-sectional view similar to that of FIG. 5 illustrating the corneal tissue after it has been treated.
Figure 6B:
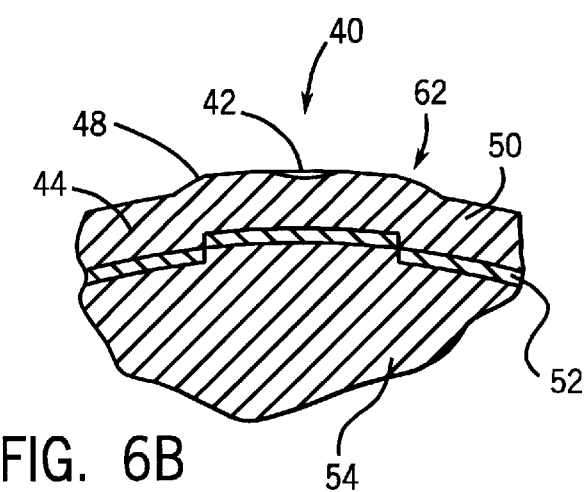
FIG. 6B is a cross-section view similar to that of FIG. 5 illustrating the corneal tissue after it has been treated and healed.

As illustrated in FIGS. 6A and 6B, a portion of the corneal tissue 44 may be deformed in a manner that moves plug portion 58 with respect to the remainder of the corneal tissue 44. Potentially, plug portion 58 can be moved inwardly with respect to eye 40 or outwardly with respect to the remainder of eye 40 as illustrated in FIG. 6A. Generally, plug portion 58 is moved slightly outwardly to correct refractive errors that lead to conditions such as hyperopia (farsightedness) or presbyopia.

As illustrated, plug portion 58 is cut from a predetermined region 62 of corneal tissue 44. By deforming a desired corneal portion 64, plug 58 is squeezed and moved slightly outwardly as illustrated in FIG. 6A. Cut 56 is then permitted to heal, thereby permanently affixing plug portion 58 in its new location with respect to the remainder of the corneal tissue 44, as illustrated in FIG. 6B.

To move plug portion 58 outwardly, it is preferred that corneal portion 64 be located proximate outer cut surface 60, preferably slightly outside and below outer cut surface 60 as indicated by each X in FIG. 6A. By shrinking this corneal portion 64 of corneal tissue 44, plug portion 58 is squeezed slightly outwardly to appropriately change the curvature of corneal surface 48. It should be noted that the necessary movement of plug portion 58 varies, depending on the type and severity of the vision disorder, but it is typically on the order of 20-80 microns. The movement illustrated in the Figures has been exaggerated merely for illustrative purposes. Also, corneal portion 64 may be within plug 58 if the desired motion of plug 58 is inward with respect to the surrounding corneal tissue. In either event, the displaced or separated intrastromal relationships recombine as the plug heals into place at its new location, thereby permanently changing the shape of the corneal surface.

The shrinking of corneal portion 64 and the consequent outward movement of plug portion 58 may be accomplished by selectively heating the corneal tissue at portion 64. Although the heating could be accomplished in a variety of ways, a laser of desired wavelength and intensity is preferably used. An example of one type of laser that has proved effective is a holmium laser. The laser energy causes corneal portion 64 of collagen layer 54 to shrink around plug portion 58 and force plug portion 58 outwardly. The effect of the laser may be enhanced by injecting a dye, such as the photodye Rose Bengal manufactured by Smith and Nephew of London, England, into the area of portion 64. Dye 66 may be injected either independently or at the time plug 58 is created by cut 56. In either event, the dye absorbs more of the laser energy creating a greater heating of region 64 with a lower energy laser. The lower energy laser tends to protect the surrounding corneal tissue. In some procedures, the laser may be of sufficiently low energy to avoid damaging the epithelium even when the epithelium is not cut and the light energy is transferred through the epithelium. This is particularly true when dye is injected at the desired area of treatment, e.g., corneal portion 64, to promote greater heating and deformation of corneal tissue at the area of treatment without changing the intact epithelial layer 50.

The epithelial layer 50 can be protected further by reducing the likelihood that the epithelium will absorb sufficient energy from the laser, infrared light source or other heat source to damage the epithelium when the energy is transferred therethrough. This can be accomplished, as explained more fully below, by physically cooling the epithelium as energy is directed to corneal portion 64. The epithelial layer 50 also can be protected by selectively displacing the primary, naturally occurring water ($H_2O$) from a portion of the epithelium with a material that does not absorb heat energy from the laser, infrared heat lamp or other energy source.

Preferably, the laser light energy is split into multiple beams of light, e.g., eight, which are evenly spaced about plug 58 to cause uniform, simultaneous deformation of corneal tissue. It is also preferred that the heating be accomplished at the same time or shortly after plug 58 is cut to avoid swelling, hydration and detrimental changes to the cut corneal tissue.

Figure 7:
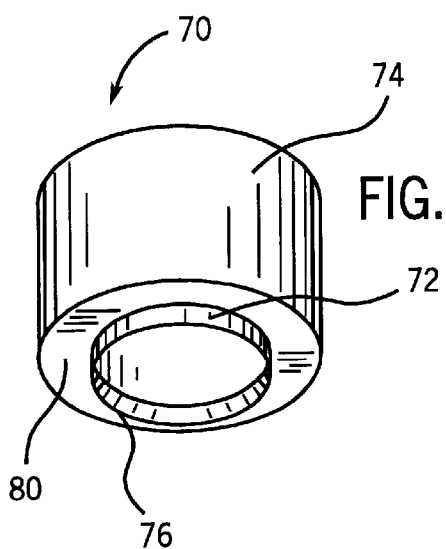
FIG. 7 is a perspective representation of a cutting device according to a preferred embodiment of the invention.
Figure 8:
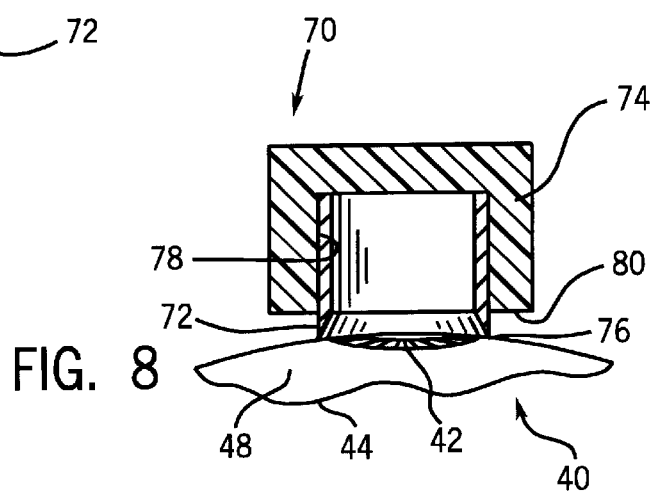
FIG. 8 is a cross-sectional view of the device illustrated in FIG. 7 and disposed adjacent an eye.

Referring generally to FIG. 7, an apparatus 70 for reshaping predetermined region 62 of corneal tissue 44 is illustrated. Apparatus 70 includes a cutter 72 and a guard 74. Cutter 72 is preferably a blade, such as a trephine blade made from an appropriate metal, such as surgical steel. Cutter 72 is mounted to guard 74 and includes a cutting edge 76 (See FIGS. 7 and 8) designed to cut substantially about the perimeter of pupil 42 at a given radius to create plug 58. In the most preferred embodiment, cutting edge 76 has a generally circular configuration.

Guard 74 preferably has a hollow interior 78 designed to receive cutter 72. The exact configuration can vary substantially without departing from the scope of the present invention, and cutter 72 may be fixedly mounted or adjustably mounted to permit retraction of cutting edge 76 into guard 74. However, during the cutting operation illustrated in FIG. 8, cutting edge 76 is maintained at a predetermined distance from a leading edge 80 of guard 74. Thus, cutting edge 76 should remain fixed with respect to leading edge 80 during the cutting operation. In some applications, the distance between leading edge 80 and cutting edge 76 may vary at different points, but the predetermined distance at each point remains the same during the cutting operation.

Cutting edge 76 extends at least 50 microns and up to 800 microns from leading edge 80. Typically, cutting edge 76 extends at least 50 microns and up to 200 microns. The exact distance is determined according to the type of vision disorder and the severity of that disorder. If a laser is used to cut the corneal tissue, the predetermined distance can precisely be controlled by controlling the intensity of the laser.

In the Figures, cutter 72 is exemplified by a circular trephine cutter, but a variety of cutters could be used. For example, certain lasers could potentially be used to provide cut 56 and create plug 58. An example is an excimer laser, such as those manufactured by the Laser Sight Company of Orlando, Fla., U.S.A. Movable blades could also be used to create cut 56 either fully or partially about the perimeter of pupil 42.

Figure 9:
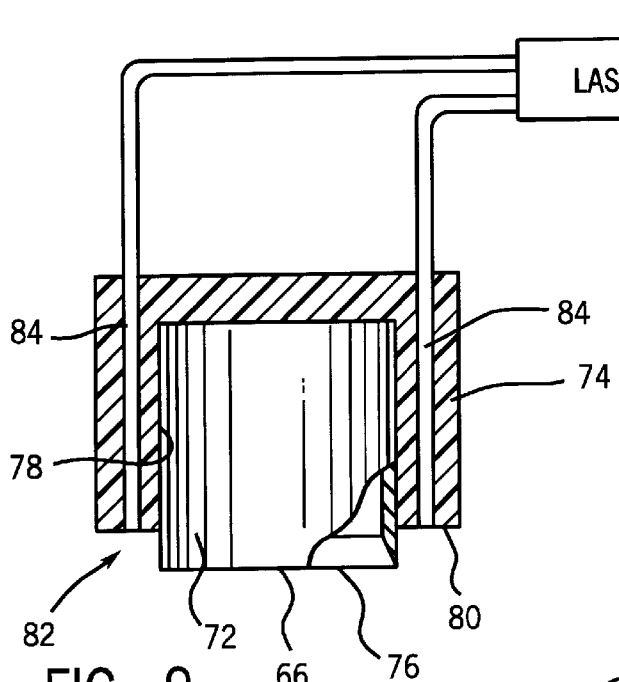
FIG. 9 is a side view of another exemplary device used for cutting and altering corneal tissue.
Figure 10:
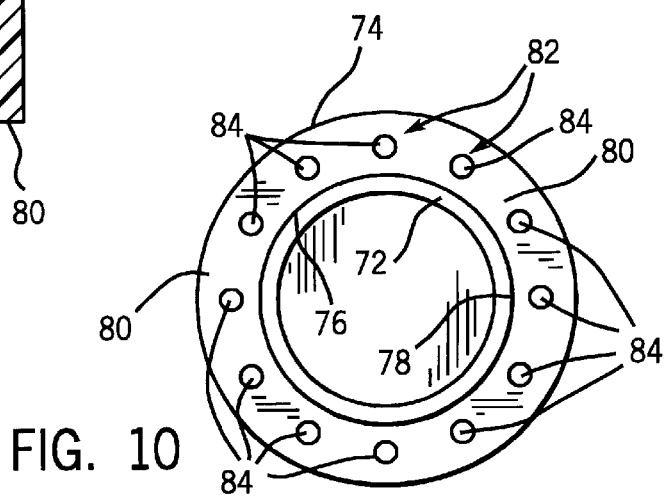
FIG. 10 is a bottom view of the device illustrated in FIG. 9.

As illustrated in FIGS. 9 and 10, guard 74 may incorporate a light transmitting material 82 capable of transmitting laser light energy through guard 74 and towards corneal portion 64 of tissue 44, preferably through cut 56. Light transmitting material 82 may be made of a variety of materials, such as quartz, sapphire or optical fibers 84, as illustrated in FIGS. 9 and 10. Optical fibers 84 are oriented to direct laser light energy, supplied by a laser light source 86, to corneal portion 64 of tissue 44. An exemplary laser is a holmium laser, such as those manufactured by Sunrise Corp. of California, U.S.A. or Summit Corp. of Massachusetts, U.S.A.

In the illustrated embodiment, the light transmitting material 82 extends through guard 74 and is uniformly disposed about leading edge 80 to provide a transfer of energy that heats corneal portion 64 in an evenly distributed manner about the circumference of plug 58. Thus, the heating of portion 64 is uniform, causing a uniform shrinking of the collagen layer proximate plug 58 to thereby precisely move plug 58 outwardly the desired amount. optionally, dye 66 may be coated on cutter 72 along cutting edge 76 to dye the corneal tissue disposed in proximity to plug 58 as cutter 72 is pressed into eye 40. As explained above, dye 66 more readily absorbs the laser light energy to provide heating, and consequent shrinking, of the collagen layer proximate plug 58. This permits the use of a lower energy laser that is less likely to harm or affect tissues other than those proximate plug 58.

As described above, cutter 72 works as a heat absorption modifier by cutting or severing the epithelial layer 50 to permit energy to be transferred to an intrastromal region, such as corneal portion 64, without passing directly through the epithelium. However, in some applications it may be advantageous to leave the epithelium intact. Avoiding cutting of epithelial layer 50 can, among other things, reduce the pain to the patient, reduce the healing time and limit the threat of infection. However, a different type of heat absorption modifier is required to avoid damage to epithelial layer 50, e.g., by excess heating, when energy is passed through the epithelium to Bowman's membrane layer 52 or other intrastromal regions, such as corneal portion 64. In some procedures, the combination of a low energy source, such as a low energy laser, can be combined with the injection of dye 66 into corneal portion 64. In these procedures, sufficient energy can be passed through epithelial layer 50 to be absorbed by dye 66 at corneal portion 64. The absorption of energy by the dye provides sufficient heating to obtain the desired deformation of corneal tissue at corneal portion 64.

Figure 11:
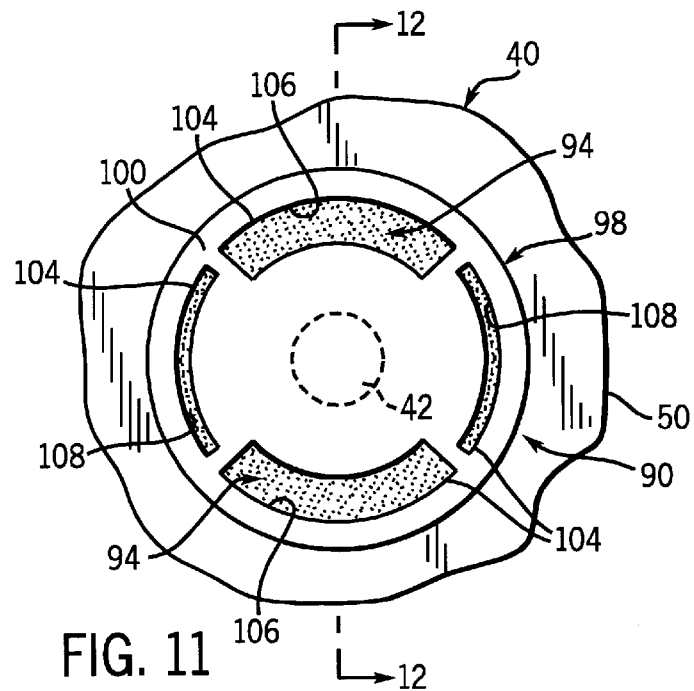
FIG. 11 is a front view of an eye with an alternate heat absorption modifier.
Figure 12:
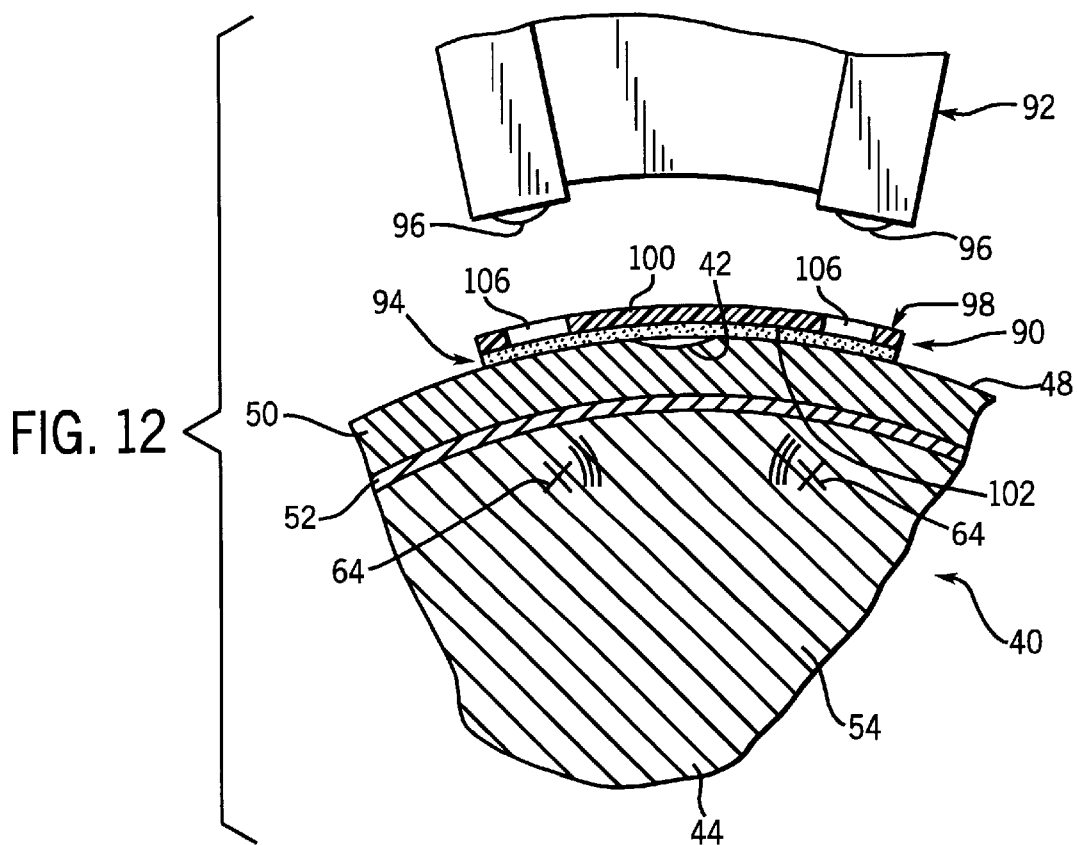
FIG. 12 is a cross-sectional view taken generally along line 12—12 of FIG. 11 and also showing a heater device according to one embodiment of the invention.

However, it is typically necessary to provide an additional heat absorption modifier. As illustrated in FIGS. 11 and 12, an alternate heat absorption modifier 90 can be used in combination with an energy emitting device 92.

In one embodiment of heat absorption modifier 90, a material 94 is placed against the outer surface of epithelial layer 50. Material 94 may include an appropriate isotope, preferably in liquid form, that is formulated to displace the primary, naturally occurring water ($H_2O$) in epithelial layer 50. The displacement of this water limits the epithelial layer's absorption of certain types of energy emitted from energy emitting device 92 and passed through epithelial layer 50 to a predetermined treatment area of corneal tissue, such as corneal portion 64. Exemplary materials 94 include isotopic variants of the $H_2O$ isotope most commonly present in tissue. Exemplary materials that function as an energy absorption modifier include deuterium oxide ($D_2O$) or tritium oxide ($H_3O$). When such materials are used, energy may be emitted from energy emitting device 92 in the form of laser light or lamps emitting electomagnetic radiation in the infrared region. Device 92 typically is of the type that emits energy via one or more energy emitters 96, e.g. light emitters, which direct energy through epithelial layer 50 to predetermined treatment area 52,64. For example, energy emitter 92 may comprise a Nd:Yag laser having a wavelength of approximately 1320 nanometers. Energy emitter 92 also can comprise a CO laser emitting electromagnetic radiation having a wavelength in the range from approximately 2000 to 7000 nanometers. Alternately, energy emitter 92 can be a non-laser light emitter, such as an infrared light emitter and specifically a pulsed infrared lamp. For example, energy emitter 92 may include a mercury/CO lamp capable of emitting electromagnetic radiation having a wavelength in the range from approximately 2000 to 7000 nanometers. The intensity of the energy emitted will depend on the type of procedure and the amount of corneal tissue deformation required for the correction of eye 40.

As illustrated, energy absorption modifying material 94 is preferably combined with or formed as part of a fixture 98. Fixture 98 includes a guard portion 100 that has an inner contoured surface 102 configured to generally match the contour of outer surface 48 of eye 40. Guard portion 100 may be formed similarly to a soft contact lens and be made from materials such as methaphilcon or viflicon. Guard portion 100 is able to help hold material 94 against epithelial layer 50 as material 94 is absorbed by epithelial layer 50 to displace the naturally occurring water within the epithelial layer 50, at least in the regions of the epithelium through which energy from energy emitter 92 will pass.

In the illustrated embodiment, guard portion 100 is shown as separate from energy emitter 92, however, guard portion 100 also can be constructed as an integral part with or mounted to energy emitter 92 to ensure proper centration and registration with the patient's eye 40. Additionally, guard portion 100 preferably includes one or more fenestrations 104 that permit energy from energy emitter 92 to freely pass through guard portion 100. The use of guard portion 100 also allows treatment of the patient's eye 40 to be customized to the patient's cornea. Fenestrations 104 can be asymmetric openings for the treatment of astigmatism and other irregularities of the cornea curvature by allowing more shrinkage along one axis versus another axis. For example, as illustrated best in FIG. 11, fenestrations 104 may include a pair of wider openings 106 and a pair of narrower openings 108. Thus, more energy from energy emitter 92 is allowed to freely pass through wider openings 106 to the desired treatment area, e.g. portion 64, than through narrower openings 108, thereby causing greater shrinkage of tissue along the ninety degree axis than along the one hundred eighty degree axis.

It will be understood that the foregoing description is of preferred exemplary embodiments of this invention and that the invention is not limited the specific forms shown. For example, the system may be utilized on bodily tissues other than those of the eye or skin. Also, the use of a water displacement material/energy absorption modifier can be combined with an appropriate dye injected at the treatment area of eye or skin. Additionally, other isotopes of $H_2O$, other than deuterium oxide or tritium oxide, can be used as an energy absorption modifier to displace the primary, naturally occurring water in tissue. These and other modifications may be made in the design and arrangement of the elements without departing from the scope of the invention as expressed in the appended claims.

What is claimed is:

1. A system for modifying a predetermined area of tissue lying beneath an outer layer, the system comprising:

an energy emitter adapted to transfer energy to a predetermined area of tissue beneath an outer layer of tissue until sufficient heating occurs to deform the predetermined area of tissue; and an energy absorption modifier that is applicable to the outer layer of tissue to limit heat build up therein during heating of the predetermined area, the energy absorption modifier comprising a material that displaces the water in the outer layer of tissue to facilitate transfer of the energy therethrough.

2. The system as recited in claim 1, wherein the outer layer of tissue is an epidermal layer.

3. The system as recited in claim 1, wherein the outer layer of tissue is an epithelial layer.

4. The system as recited in claim 1, wherein the material includes deuterium oxide.

5. The system as recited in claim 1, wherein the material includes tritium oxide.

6. The system as recited in claim 1, wherein the energy emitter comprises a laser.

7. The system as recited in claim 6, wherein the laser is an Nd:Yag laser.

8. The system as recited in claim 1, wherein the energy emitter comprises an infrared lamp.

9. The system as recited in claim 1, further comprising a fixture that may be placed against the outer layer of tissue to act as a heat sink.

10. The system as recited in claim 9, wherein the fixture is contoured to rest against an outside surface of an epithelial layer of an eye.

11. The system as recited in claim 10, wherein the fixture includes at least one fenestration through which the light passes prior to entering the predetermined area.

12. The system as recited in claim 1, wherein the material includes an isotopic liquid.

* * * * *